United States Patent [19]

Yasukawa et al.

[11] Patent Number: 5,144,616

[45] Date of Patent: Sep. 1, 1992

[54] LASER DIODE AND MULTIBEAM OPTICAL HEAD USING THE LASER DIODE

[75] Inventors: Kaoru Yasukawa; Kiichi Ueyanagi, both of Kanagawa, Japan

[73] Assignee: Fuji Xerox Co., Ltd., Tokyo, Japan

[21] Appl. No.: 492,453

[22] Filed: Mar. 13, 1990

[30] Foreign Application Priority Data

Mar. 14, 1989 [JP] Japan .................................. 1-059564

[51] Int. Cl.5 .............................................. G11B 7/00
[52] U.S. Cl. .................................... 369/122; 369/121; 369/112
[58] Field of Search .................... 372/50, 45; 369/112, 369/121, 122

[56] References Cited

U.S. PATENT DOCUMENTS 4,298,974 11/1981 Tsunoda et al. .
4,594,719 6/1986 Ackley .................................. 372/50

FOREIGN PATENT DOCUMENTS 0092420 10/1983 European Pat. Off. .

Primary Examiner—Roy N. Envall, Jr.
Assistant Examiner—Robert Chevalier
Attorney, Agent, or Firm—Finnegan, Henderson, Farabow, Garrett & Dunner

[57] ABSTRACT

An optical information reading and writing system, comprising an optical recording medium and a multibeam optical head optically coupled to the optical recording medium. The optical recording medium has a plurality of uniformly spaced tracks in a radial direction of the medium for recording information thereon. The multibeam optical head is movable in the radial direction of the medium and includes a laser diode and an image forming optics. The laser diode has a plurality of nonuniformly spaced lasing elements in a straight line for generating a plurality of spaced laser beams. The image forming optics directs each laser beam onto a respective tracks of the optical recording medium. The spacing between the adjacent laser beams on the tracks corresponds to the spacing between the adjacent lasing elements.

13 Claims, 15 Drawing Sheets

LASER DIODE AND MULTIBEAM OPTICAL HEAD USING THE LASER DIODE

BACKGROUND OF THE INVENTION

The present invention relates to an optical writing and reading system having a laser diode and a multibeam optical head. The optical writing and reading system optically writes, reads, and deletes information by irradiating convergent rays from a light source onto an optical writing medium.

Along with the development of information processing systems in recent years, it has been strongly desired that a high transfer data rate be attained in optical writing and reading systems, in addition to realization of a large capacity, whereby the writing and reading of information is accomplished. Various efforts have been made towards this goal (as observed in 4p-ZD-1, 4p-ZD-2, etc., read at Extended Abstracts, The 49th Autumn Meeting, 1989, The Japan Society of Applied Physics). In this regard, the adoption of a multibeam optical head has been proposed in which a plurality of writing and reading converging light beam spots are used in the optical head, to obtain the high transfer data rate.

An example of this type of multibeam optical head is disclosed, for example, in Japanese Patent Laid Open No. 117744/1986.

As shown in FIG. 1, such an optical head comprises a laser diode array 100 having a plurality of laser diodes therein, each diode independently controllable for its light emission. The diodes in the laser diode array 100 are arranged linearly in a straight line and spaced from one another at an equal interval, to form a unified structure. The condenser lens 101 converts the emitted light rays from the laser diode array 100 into collimated parallel rays. An object lens 102 converges the collimated parallel rays into a plurality of beam spots. A polarizing beam splitter 103 separates incident rays from reflected rays. A plurality of beam splitting and detecting means 104 detects signals by splitting the reflected rays from the plurality of beam spots. A photo-detector 105 detects the position of one track. A pair of focusing error detecting systems 106 detect focusing errors.

Referring to FIG. 2, with this construction, it is possible to perform the writing or reading of information on a plurality of tracks 111 at the same time, by irradiating a plurality of beam spots 107, 108, and 109 (three spots in the example shown in FIG. 2) onto the plurality of tracks 111 on an optical disk 110 (shown in FIG. 1) at the same time.

Referring to FIG. 3, in the above multibeam optical head, if an attempt is made to arrange the plurality of beam spots 107, 108, and 109 linearly spaced from one another at an equal interval along a line in a radial direction A of the optical disk 110, it would be necessary to make the spacing between adjacent ones of the plurality of laser diodes arranged in the laser diode array very small due to such consideration as magnification of the optical system.

As a result, it would virtually be impossible to manufacture such a laser diode array. Therefore, as shown in FIG. 4, a plurality of beam spots 112 through 120 are arranged in a straight line, and the straight line is inclined at a prescribed angle $\theta$ with respect to the radial direction A of the optical disk 110, such that the space intervals between the adjacent laser diodes in the laser diode array 100 be set at a value practical for manufacture of the laser diode array.

However, as mentioned above, in the above multibeam optical head, the plurality of beam spots 112 through 120 are linearly arranged on a straight line and spaced at an equal interval, and the straight line is inclined at the angle $\theta$ with respect to the radial direction A of the optical disk 110, as shown in FIG. 4. As a result, it would not be possible to position all of the plurality of beam spots 112 through 120 on the tracks 111 of the optical disk 110, since each of the tracks 111 comprises an arc having a prescribed radius of curvature, resulting that the beam spots on both ends of the straight line are positioned off the tracks 111.

Consequently, it would not be possible that all the beam spots track their respective tracks 111 at the same time with accuracy even if a tracking servo is applied to the optical head. This creates a serious problem in that the writing or reading of information could not be performed on the plurality of tracks 111 at the same time.

SUMMARY OF THE INVENTION

Therefore, the present invention is to overcome the abovementioned problem of the prior art. An object of this invention is to provide a laser diode capable of tracking a plurality of laser beams each on a corresponding individual track and capable of writing or reading information on a plurality of tracks at the same time, and a multibeam optical head having such a laser diode.

According to the present invention, the multibeam optical head composed of a plurality of independently drivable light emitting diodes arranged in a straight line, wherein the plurality of light emitting spots are arranged at varying intervals.

Moreover, the multibeam optical head according to the present invention includes a laser diode having a plurality of independently drivable light emitting elements arranged at varying intervals in a straight line to generate a plurality of light beams, and an image forming optical system which forms images by directing the plurality of light beams from the laser diode onto an optical writing media in such a way that a plurality of beam spots are arranged linearly at a prescribed angle with respect to a radial direction of the optical writing media and that the interval between each pair of adjacent beam spots varies.

Regarding the manner of forming the beam spots, one of the beam spots is positioned coincident with an axis of movement of the optical head in the radial direction of the optical writing media while the remaining beam spots are positioned split in equal numbers on opposite sides of the axis of movement, when the number of the beam spots is an odd number.

When the number of the beam spots is an even number, the entire plurality of beam spots are positioned split in equal numbers on opposite sides of the axis.

However, the manner of forming the beam spots is not limited to the above described manners. It is, of course, feasible that one beam spot is positioned on the axis and the remaining beam spots are positioned on either side of the axis.

Further, for error detection of the tracking servo, it is desirable to obtain a basis, from a reflected ray of the beam spot positioned on the axis when the number of the beam spots is an odd number; but from the reflected ray of the beam spot nearest to the path, when the number of the beam spots is an even number.

Furthermore, in order to separate a beam spot from the plurality of beam spots for error detection of the tracking servo, a pin hole, for example, is used.

The multibeam optical head of the present invention includes a laser diode having a plurality of light emitting elements are arranged in a straight line and the space interval between each of the adjacent light emitting elements varies. It is therefore possible to irradiate all of the laser beams emitted from the plurality of light emitting elements on all of the corresponding tracks of the optical writing media by varying the intervals of the plurality of light emitting elements by prescribed amounts, depending on the curvatures of the corresponding tracks, even when all of the laser beams are irradiated on the corresponding tracks at the same time.

Further, the multibeam optical head of the present invention further includes an image forming optical system which forms images by directing the laser beams from the laser diode to optical writing media such that the plurality of beam spots are arranged linearly at a prescribed angle with respect to the axis of movement of the optical writing media in the radial direction and to the intervals between the adjacent beam spots are varied. The multibeam optical head is capable of forming the beam spots by focusing all of the laser beams emitted from the laser diode on the tracks on the optical writing media at the same time even when all of the laser beams are irradiated at the same time to form the beam spots arranged linearly at the prescribed angle.

DETAILED DESCRIPTION OF THE PREFERRED EMBODIMENTS

Preferred embodiments of the present invention will now be described with reference to the accompanying drawings.

Figure 5:
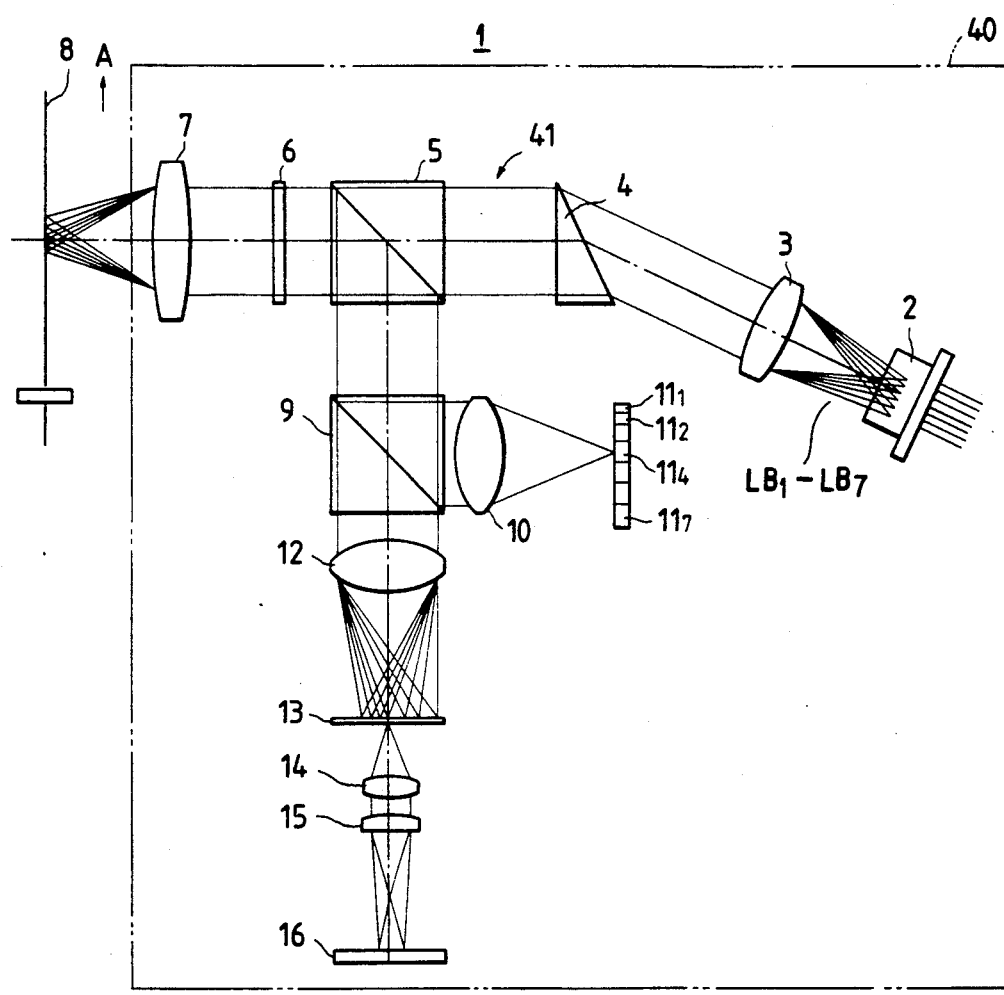
FIG. 5 and FIG. 6 are a construction view and a perspective view of the optical writing and reading system, respectively.
Figure 6:
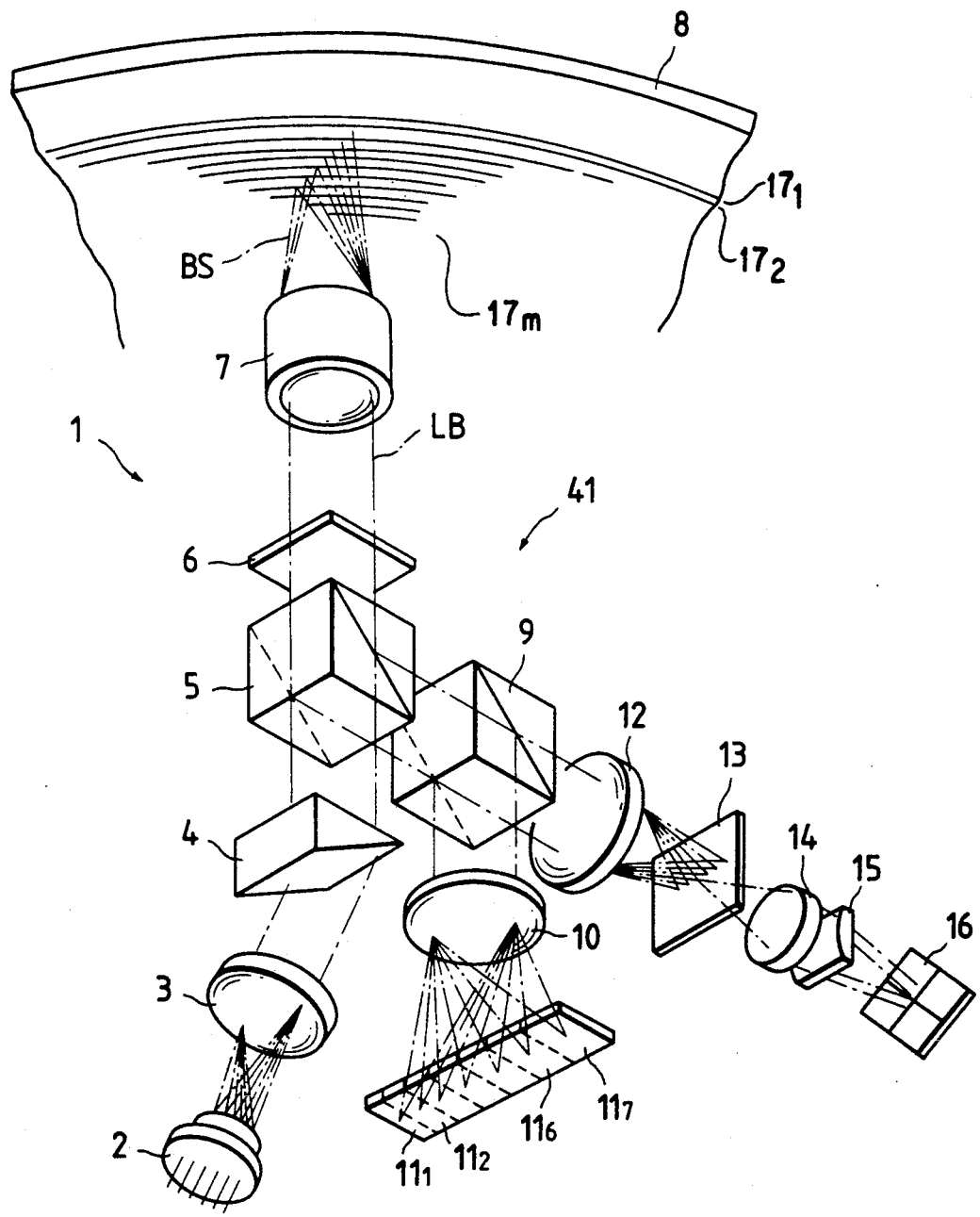

FIG. 5 and FIG. 6 illustrate a schematic and a perspective view of an optical writing and reading system respectively, comprising the laser diode and the multibeam optical head of the present invention are applied.

An optical writing and reading system 1 comprises a multibeam optical head 40 and a optical writing medium 8. The multibeam optical head 40 includes a laser diode 2 having a plurality of independently drivable light emitting elements arranged on a straight line, to generate a plurality of laser beams LB through LB, each having a cross section of an elliptic shape and an image forming optical system 41.

The image forming optical system 41 comprises a collimator lens 3, which converts the laser beams $LB_1$ through $LB_7$ into an equal number of parallel rays; a beam shaping prism 4, which conditions the parallel rays; into circular sectional shape, a polarizing beam splitter 5, which separates the conditional parallel rays which are to be irradiated on the optical disk 8 from light rays reflected from the optical disk 8; a one-quarter wavelength plate 6, which converts linearly deflected rays into circularly deflected rays and vice versa; an object lens 7, which converges and irradiates the light rays from the one-quarter wavelength plate 6 onto the optical disk 8; a beam splitter 9, which splits into two parts the reflected light rays separate by the polarizing beam splitter 5; a condenser lens 10, which collects one part of the reflected light rays from the beam splitter 9; photo-detector elements $11_1$ through $11_7$, which receive the one part of the reflected light rays from the condenser lens 10; a condenser lens 12, which collects the other part of the reflected light rays from the beam splitter 9; a pinhole 13, which permits the passage of only one of the a reflected light rays corresponding to the middle laser beam $LB_4$ of the laser beams $LB_1$ through $LB_7$ collected by the condenser lens 12; a condenser lens 14 and a cylindrical lens 15, which detect a focusing error signal by applying the astigmatic method to the light ray permitted to pass through the pinhole 13; and a photo-detector element 16, which receives the permitted light ray beam from the condenser lens 14 and cylindrical lens 15.

Figure 1:
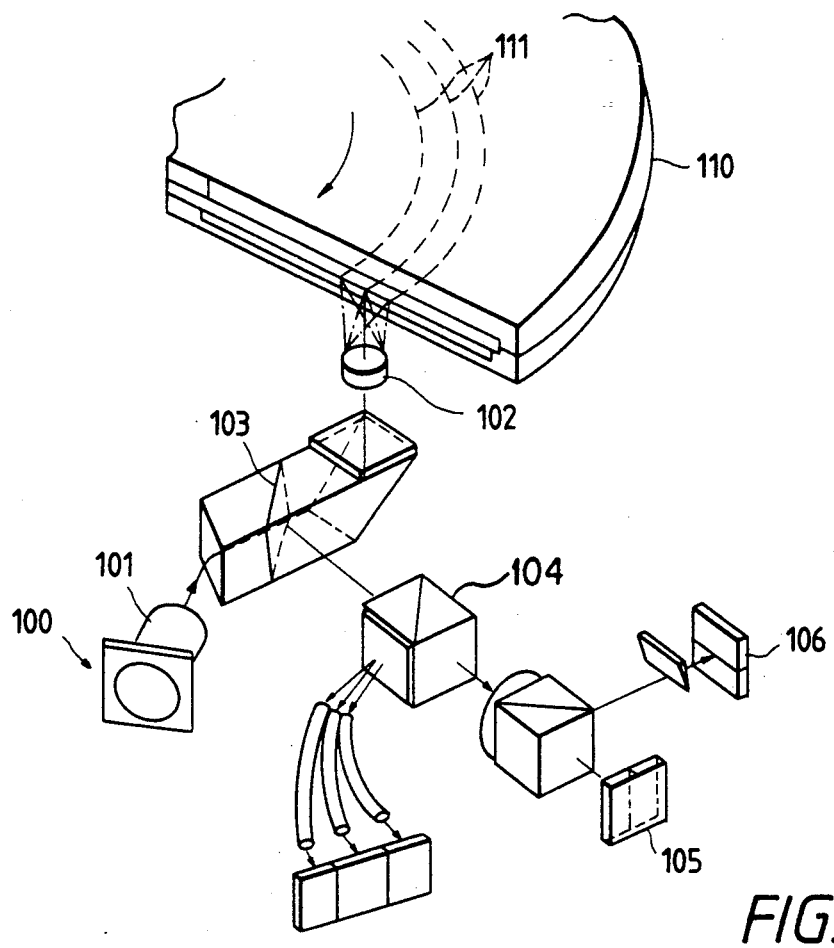
FIG. 1 is a perspective view showing a conventional multibeam optical head.
Figure 2:
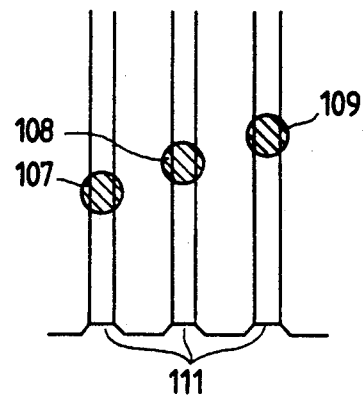
FIG. 2 is a plan view illustrating the formation of the beam spots of the multibeam optical head of FIG. 1.
Figure 3:
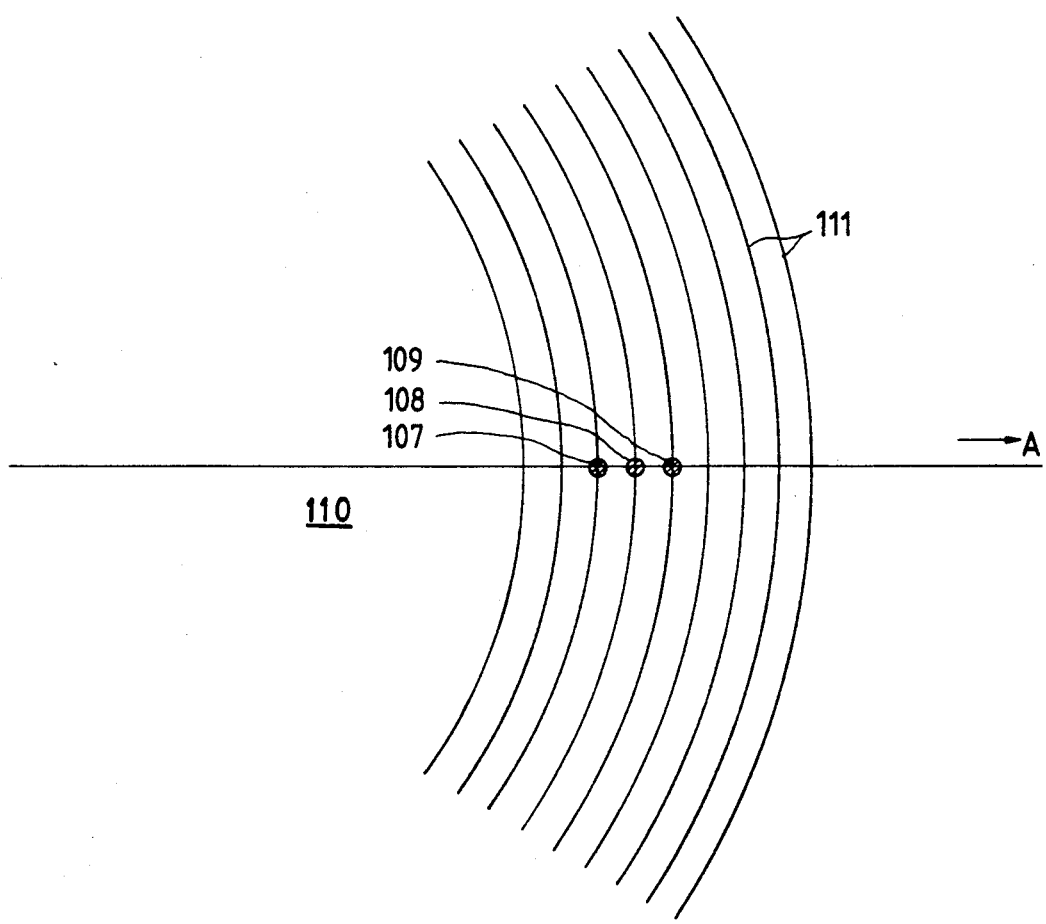
FIG. 3 is an explanatory view showing one manner of the beam spot formation with the multibeam optical head of FIG. 2.
Figure 4:
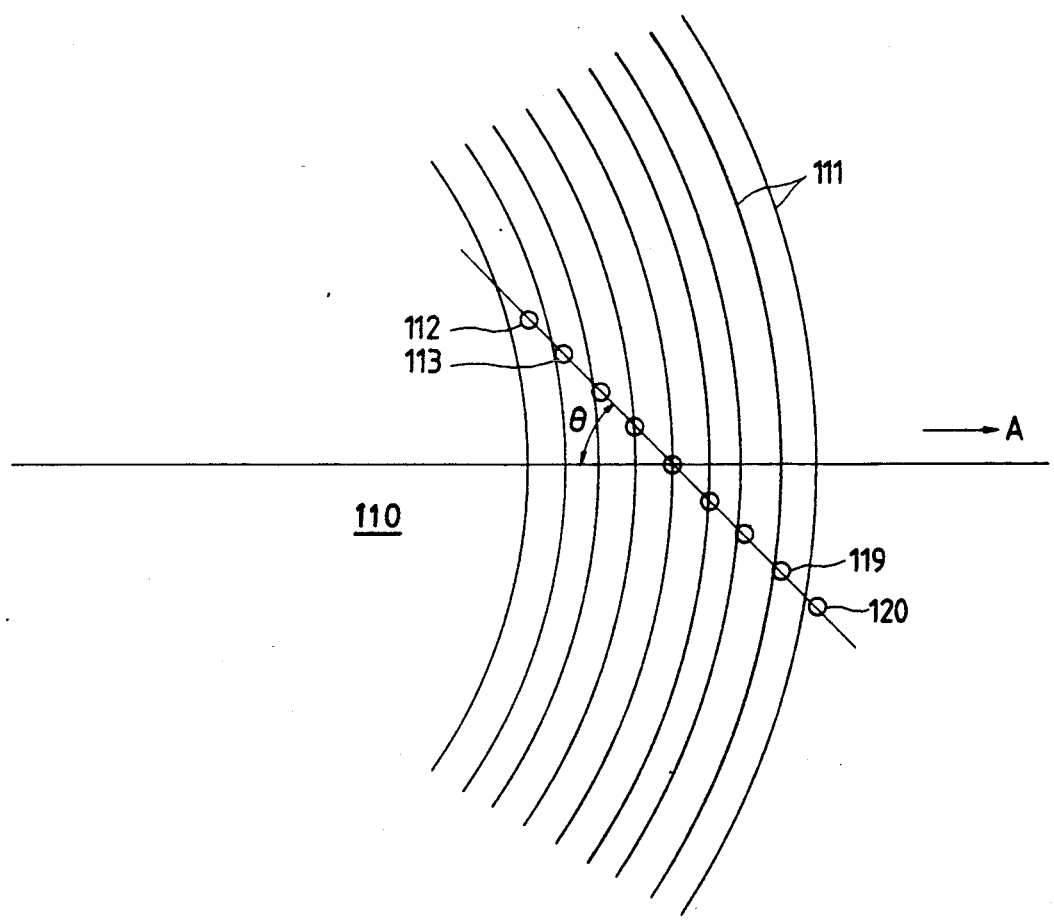
FIG. 4 is an explanatory chart showing another manner of the beam spot formation of the multibeam optical head of FIG. 1.

The optical disk 8 has a plurality of tracks $17_1$ through $17_m$ (m is a nonzero positive integer), as shown in FIG. 3, to write information thereon. Each of the tracks $17_1$–$17_m$ has a prescribed radius of curvature and a prescribed pitch p in the form of concentric circles, as shown in FIG. 6.

As described above, in the above optical writing and reading system 1, the plurality of laser beams $LB_1$ through $LB_7$, which are emitted in an elliptical shape from the laser diode 2, are converted into the equal number of parallel rays by the collimator lens 3, and thereafter shaped into circular beams by the beam shaping prism 4. After that, these circular beams corresponding to the laser beams $LB_1$ through $LB_7$ pass through the polarizing beam splitter 5 and the one-quarter wavelength plate 6. These beams are further narrowed down by the object lens 7 and irradiated on the tracks $17_1$–$17_m$ on the optical disk 8.

The light rays reflected from the tracks $17_1$–$17_m$ of the optical disk 8 are fed into the multibeam optical head 40 through the same path in a reverse order as mentioned above. The light rays are reflected and at the same time split by the beam splitter 9 to travel in two directions. The reflected light rays corresponding to the laser beams $LB_1$ through $LB_7$ in one stream are applied by the condenser lens 10 onto seven photo-detector elements $11_1$ through $11_7$ to form images corresponding the image information recorded on the tracks 17 through $17_7$, and read at the same time by the photo-detector elements $11_1$ through $11_7$.

Figure 7:
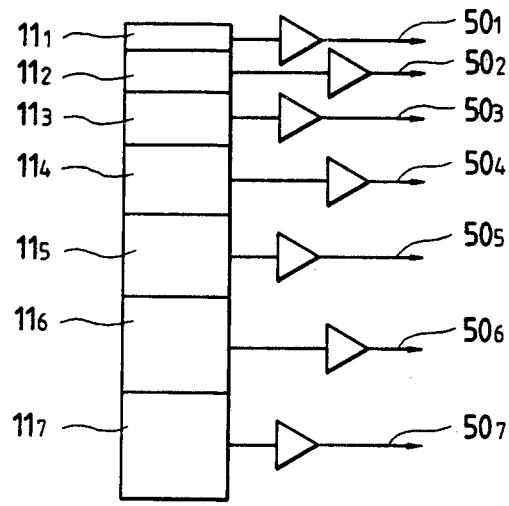
FIG. 7 is a circuit diagram showing the detecting section for the tracking error signal.

As shown in FIG. 7, the individual photo-detector elements $11_1$ through $11_7$ are connected with differential amplifiers, and the image information is obtained as output signals $50_1$ through $50_7$ from the individual differential amplifiers.

Referring to FIG. 5, the reflected rays corresponding to the laser beams $LB_1$ through $LB_7$, forming the other stream after split by the beam splitter 9 mentioned above, are condensed by a condenser lens 12, and thereafter only the reflected light ray corresponding to the middle laser beam $LB_4$ passes through the pinhole 13 and is applied to form its image onto the photodetector element 16 by the condenser lens 14 and the cylindrical lens 15, to obtain a tracking error signal whereby a focusing error signal is obtained by the astigmatic process.

Figure 9:
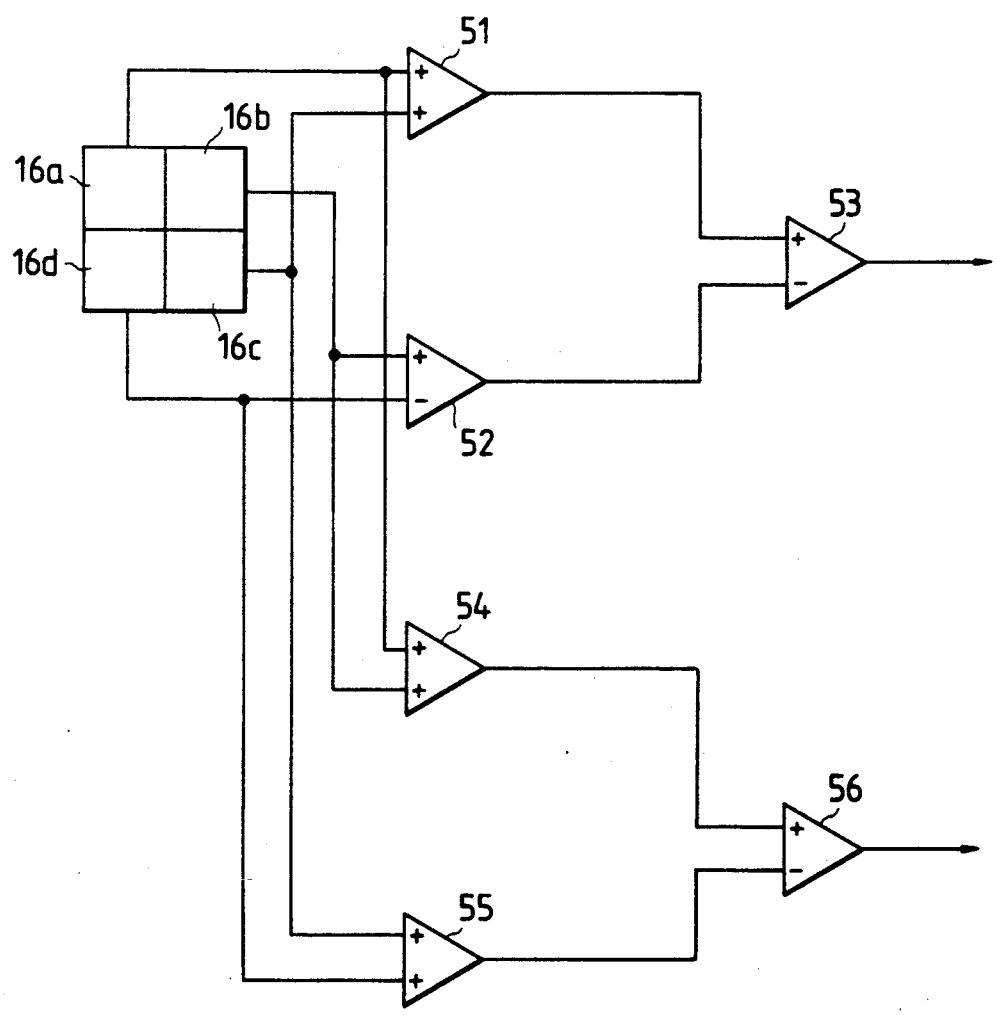
FIG. 9 is a circuit diagram showing the detecting section for the focusing error signal.

More specifically, referring to FIG. 9 and FIG. 10, the photo-detector element 16 comprises a pair of adjacent photoreceptor elements 16a and 16b and a pair of adjacent photoreceptor elements 16c and 16d, which are connected to adding amplifiers 54 and 55, respectively. The adding amplifiers 54 and 55 are connected to a differential amplifier 56. The tracking error signal is obtained from the differential amplifier 56.

Figure 8:
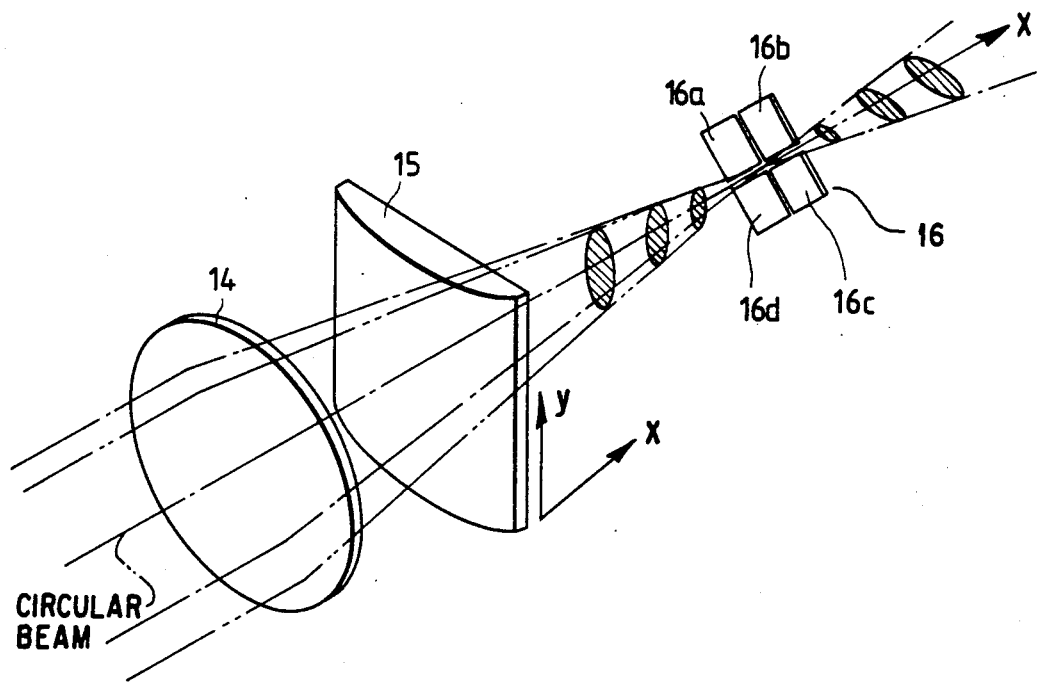
FIG. 8 is a perspective view showing the principle of the detection of the focusing error signal.

The astigmatic process to obtain the focusing error signal is explained in reference to FIG. 8 and FIG. 9 below. Referring to FIG. 5, a circular beam is obtained in an approximately midway position in an in-focus state by varying the focus in the x-axis direction and that in the y-axis direction of the laser beam by means of the cylindrical lens 15. The quadrant photo-detector element 16 comprises the diagonally positioned photo-detector elements 16a and 16c and the diagonally positioned photo-receptor elements 16b and 16d. Referring to FIG. 10, the photo-receptor elements 16a and 16c are connected to adding amplifiers 51, and the photo-receptor elements 16b and 16d to 52. The amplifiers 51 and 52 are in turn connected to a differential amplifier 53, as shown in FIG. 9.

Figures 10A, 10B, 10C:
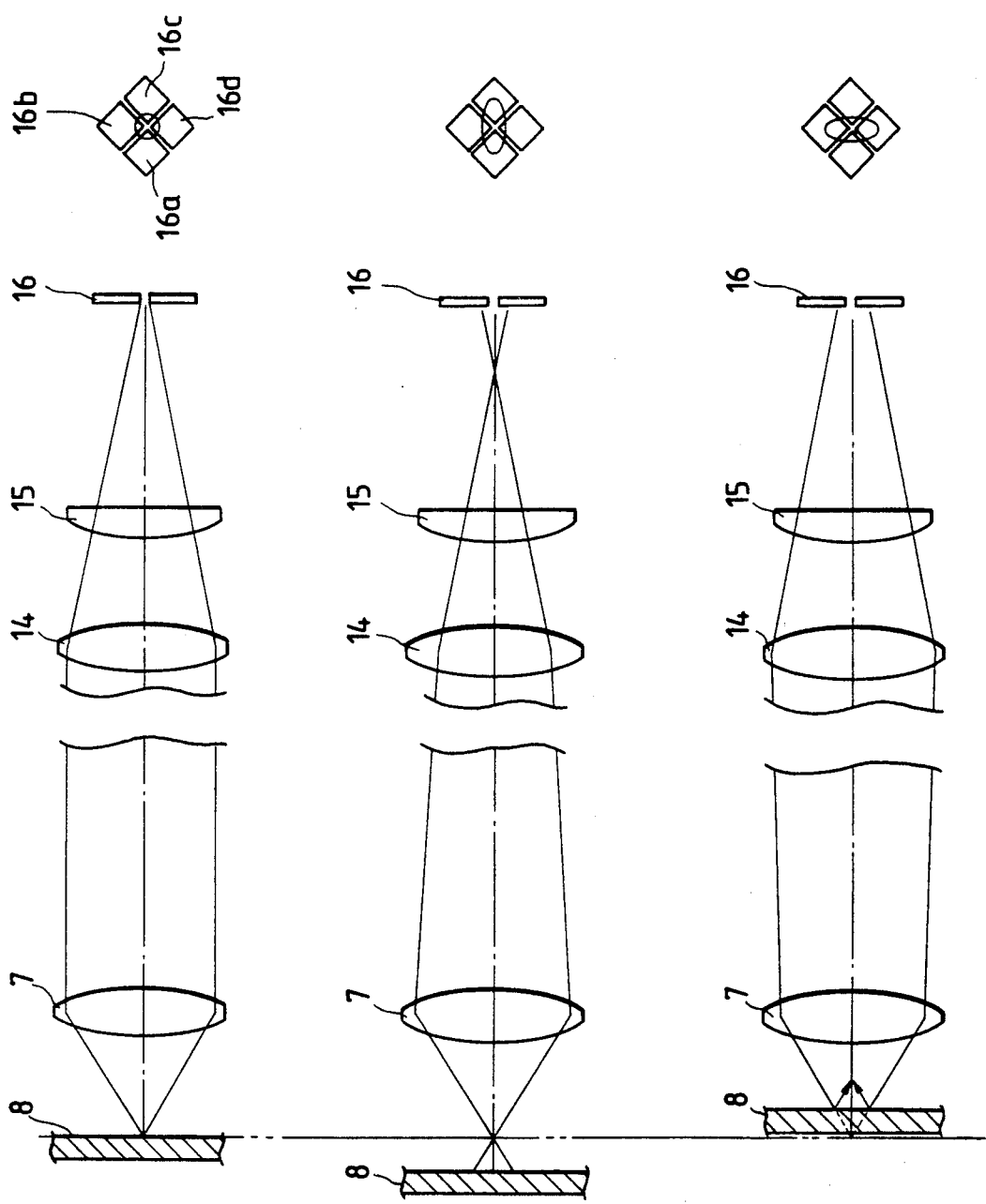
FIGS. 10(a), 10(b) and 10(c) are perspective views respectively showing the detecting operations for the focusing error signal.

Referring to FIG. 10(a), the output of the differential amplifier 53 becomes zero in the in-focus state. Referring to FIG. 10(b) and FIG. 10(c), the output of the differential amplifier 53 becomes nonzero (either + or −); the focusing error signal is thereby obtained.

The laser diode of the present invention comprises a plurality of light emitting elements arranged on a straight line at varying intervals. More specifically, referring to FIG. 11, the laser diode 2 includes a plurality of laser diode elements $18_1$ through $18_7$ arranged on a straight line in that intervals $X_1$ through $X_6$ between respective adjacent laser diode elements increase progressively (i.e., $x_1 < x_2 ... < X_6$)

Figure 12:
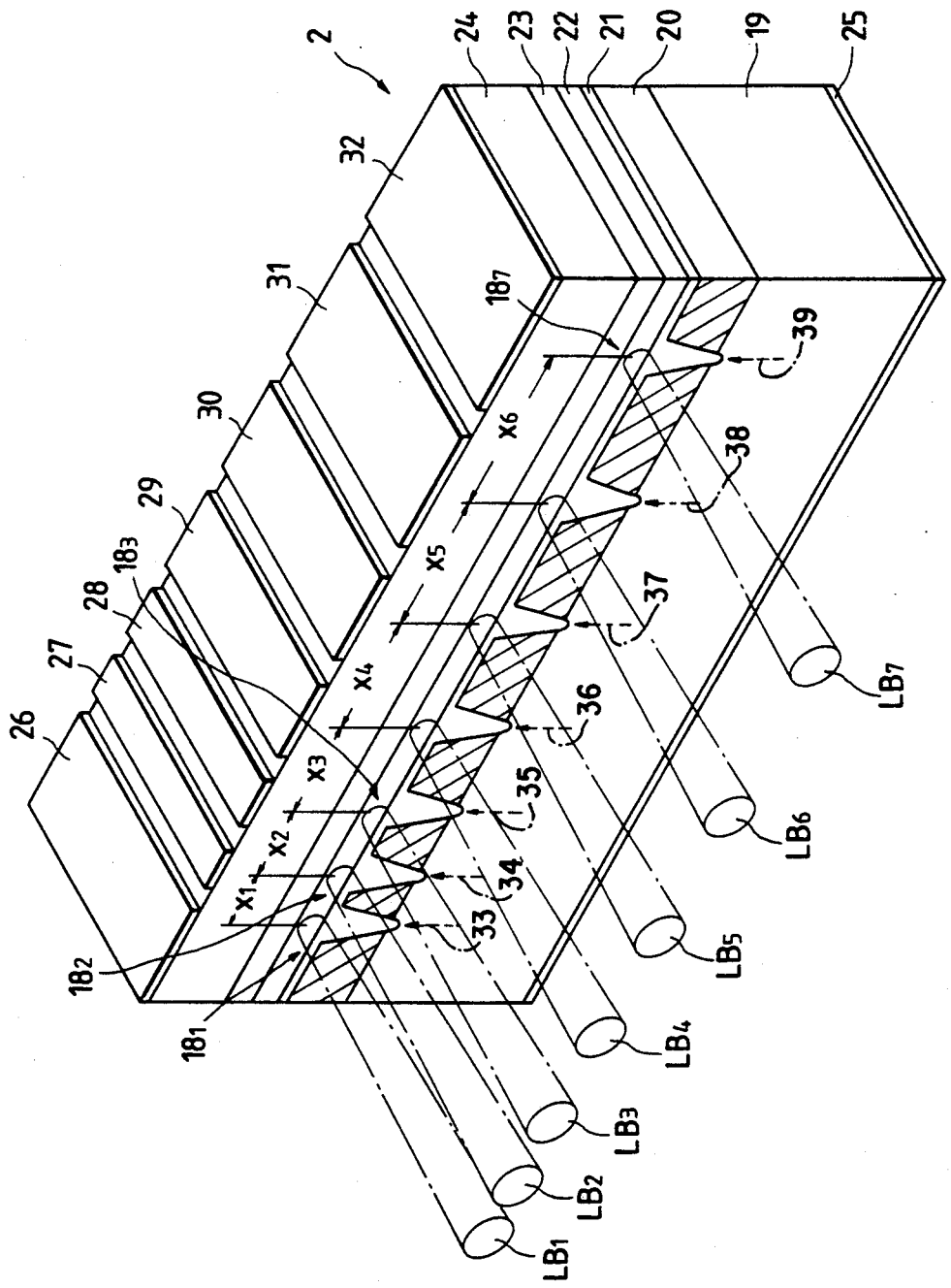
FIG. 12 is a perspective view showing the laser diode.

Referring to FIG. 12, the principle part of the laser diode 2 comprises a p-GaAs substrate 19; an n-GaAs layer 20 formed on the substrate 19 and forming a current constricting layer; a p-$Ga_{1-x}Al_xAs$ layer 21 formed on the n-GaAs layer 20 and forming a clad layer; a p-$Ga_{1-y}Al_yAs$ layer 22 formed on the p-$Ga_{1-x}Al_xAs$ layer 21 and forming an active layer; and a p-$Ga_{1-x}Al_xAs$ layer 23 formed on the p-$Ga_{1-x}Al_xAs$ layer 22 and forming a clad layer. A p-side electrode 25 is formed over the entire area on the back side of the p-GaAs substrate 19. A plurality of n-side electrodes 26 through 32 are formed on the n-GaAs layer 24. V-shaped grooves 33 through 39 formed on the n-GaAs layer 20 by the mesa-etching process or the like. The laser diode elements $18_1$ through $18_7$ are formed in individual V-shaped grooves 33 through 39, respectively.

The electric current is injected into the active area of the individual laser elements $18_1$ through $18_7$, in directions indicated by arrows and into the inside region of the current constricting n-GaAs layer 20, through the V-shaped grooves 33 through 39 by applying a driving voltage independently between the p-side electrode 25 and the n-side electrodes 26 through 32. n-GaAs layer 20 has a polarity opposite that of the substrate 19. Then, laser oscillation takes place in the p-$Ga_{1-y}Al_yAs$ layer 22, which is an active layer. The plurality of laser beams $LB_1$ through $LB_7$ of an elliptical shape are emitted from the individual laser diode elements $18_1$ through $18_7$. The laser beams $LB_1$ through $LB_7$ thus emitted are spaced at intervals equal to the intervals $X_1$ through $X_6$ of the laser diode elements $18_1$ through $18_7$, respectively.

Figure 13:
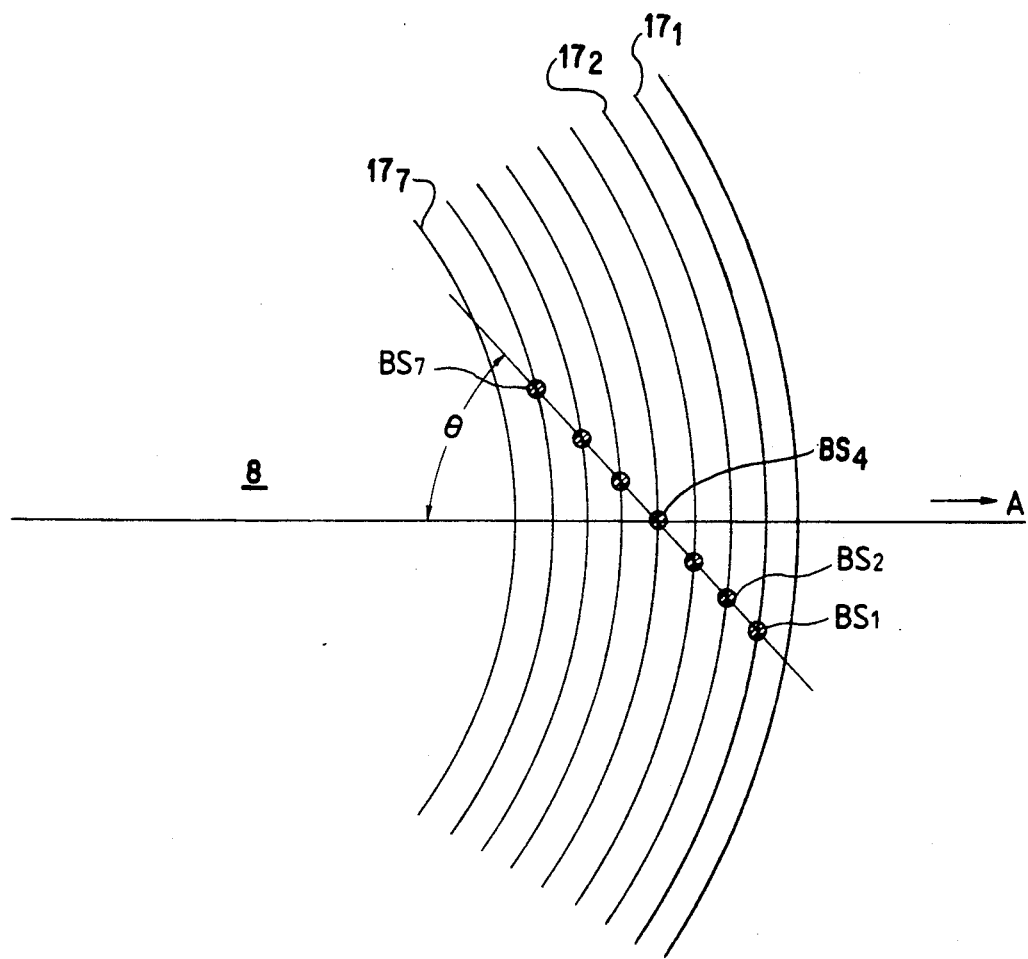
FIG. 13 is a plan view showing the state of image formation with the multibeam.

Referring to FIG. 13, the multibeam optical head of the present invention further comprises the image forming optical system 41 (shown in FIG. 5). The optical system 41 directs the plural number of laser beams $LB_1$ through $LB_7$ from the laser diode 2 onto the optical writing media 8 such that a plurality of beam spots $BS_1$ through $BS_7$ are arranged linearly at a prescribed angle with respect to a radial direction A of the optical writing media 8. The intervals between the beam spots $BS_1$ through $BS_7$ vary.

The component parts of the image forming optical system 41 constitute a main optical portion of the optical writing and reading system outside the optical disk 8, as shown in FIG. 5. The multibeam optical head 40 is movable along the line in the radial direction A of the optical disk 8, as shown in FIG. 13, by a driving means (not shown).

Referring to FIG. 5 and FIG. 13, the laser beams $LB_1$ through $LB_7$ emitted from the laser diode 2, which pass through the collimator lens 3, the anamorphic prism 4, the polarizing beam splitter 5, and the one-quarter wavelength plate 6, are converged by the object lens 7, and directed onto the optical disk 8 to form the plurality of beam spots $BS_1$ through $BS_7$ on a straight line with an angle $\theta$ with respect to the radial direction A of the optical disk 8.

Figure 11:
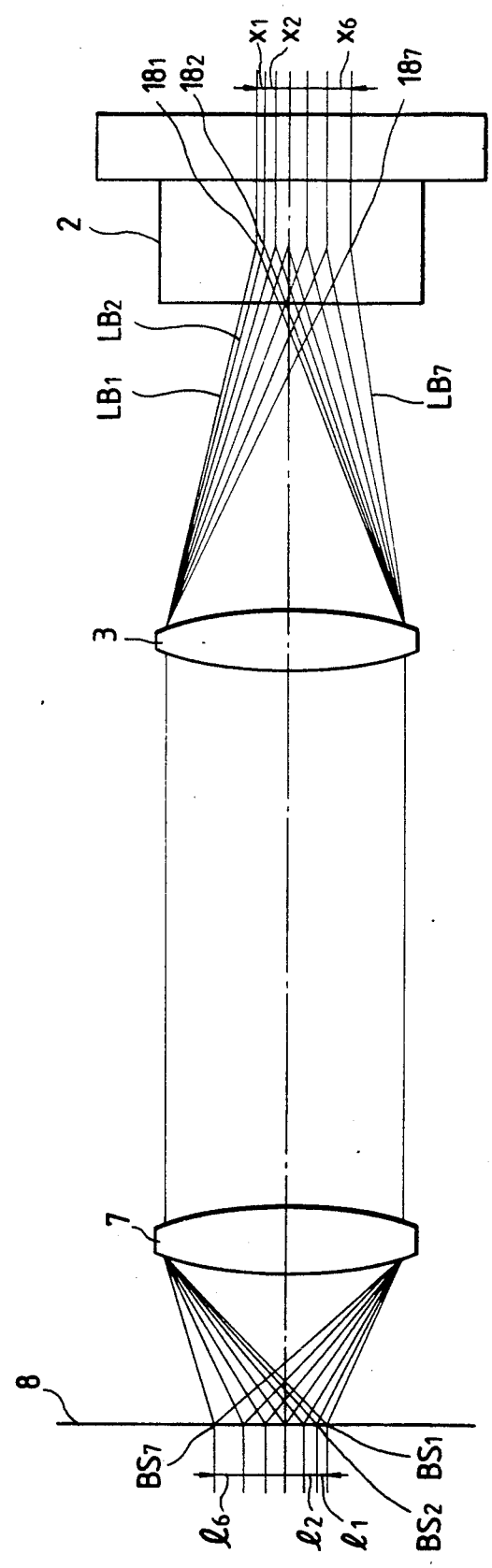
FIG. 11 is a schematic construction view illustrating one embodiment in an optical writing and reading system to which a multibeam optical head according to this invention is applied.

Referring to FIG. 11, beam spots $BS_1$ through $BS_7$ onto the optical disk 8 are spaced from one another with intervals $1_1, 1_2, \ldots 1_6$ between respective adjacent beam spots. These intervals progressively increases in the order of the position of the respective adjacent beam spots (i.e., $1_1 < 1_2 ... < 1_6$) such that each of the beam spots $BS_1$ through $BS_7$ be positioned on a respective one of the tracks $17_1$ through 17(?) of the optical disk 8, as shown in FIG. 13. In this example, the number of the beam spots $BS_1$ through $BS_7$ is seven, which is an odd number. Among the beam spots $BS_1$ through $BS_7$, a middle beam spot $BS_4$ is so arranged as to move along the radial direction A of the movement of the optical head 40, as shown in FIG. 13.

Figure 14:
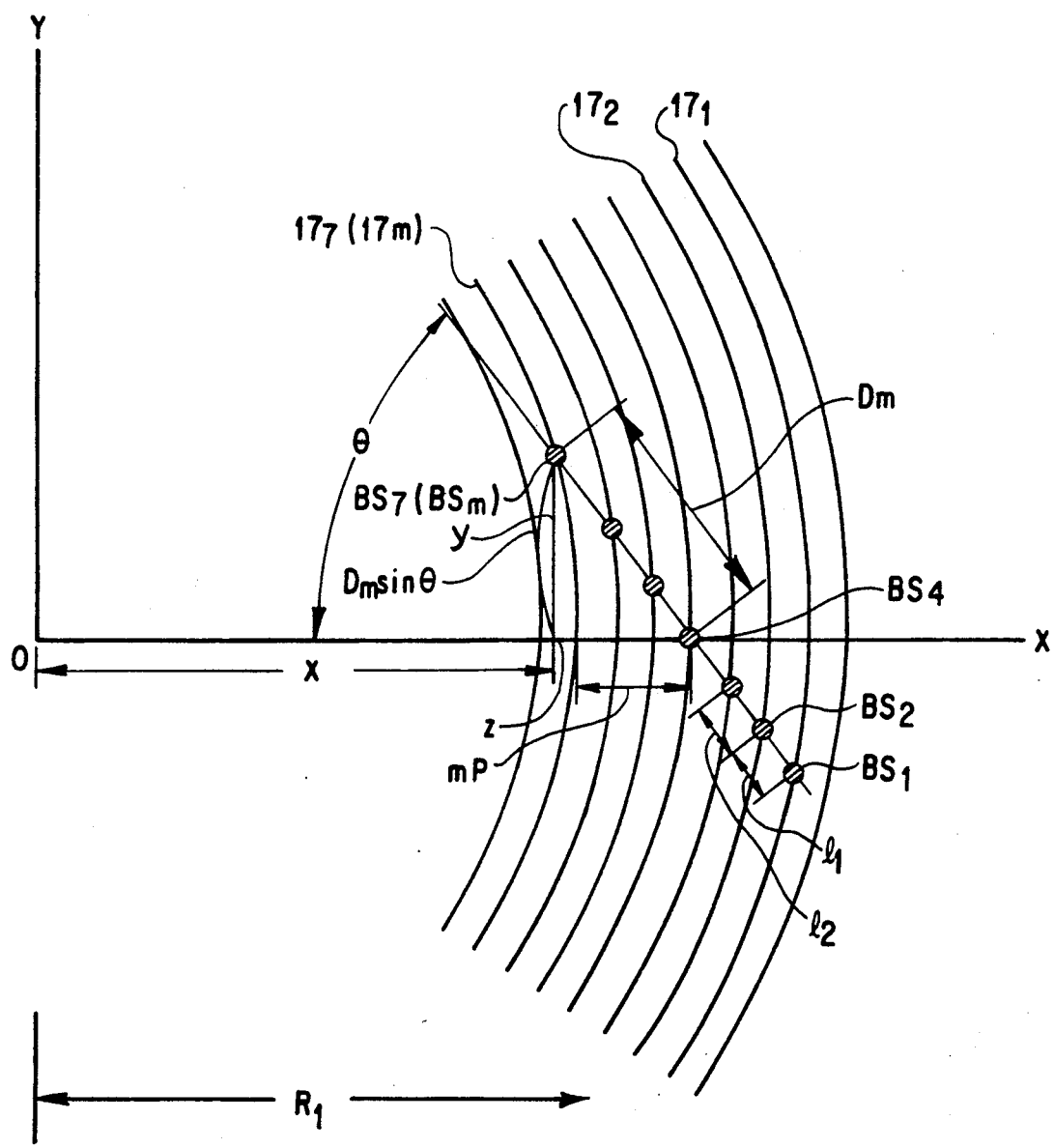
FIG. 14, is an explanatory view illustrating the method of setting the intervals of the multibeam.

The intervals $l_1$ through $l_7$ of the beam spots $BS_1$ through $BS_7$ are set as follows. Referring to FIG. 14, when the middle beam spot $BS_4$ on a track $17_4$ of the optical disk 8 moved along the radial direction A of the optical disk 8 and also to be positioned, the remaining beam spots are divided between inner side beam spots $BS_5$ through $BS_7$ and outer side beam spots $BS_1$ through $BS_3$ with respect to the beam spot $BS_4$.

The x-y positioning of a beam spot $BS_m$, which is the beam spot in the m-th position on the inner side of the middle beam spot $BS_4$ counted therefrom and on a track $17_m$ which is the m-th position on the inner side of the track counted from the middle beam spot $BS_4$ satisfies a relationship:

$$x^2 + y^2 = R_1^2 \quad (1)$$

Where $R_1$ represents the radius of the track $17_m$, X the X coordinate of $BS_m$ and y the y coordinate of $BS_m$.

Referring to FIG. 14, a difference Z between the radius $R_1$ of the track $17_m$ and the x-coordinate of the beam spot $BS_m$ and a distance $D_m$ from the middle beam spot $BS_4$ to the beam spot $BS_m$ are incorporated into the equation (1) to yield:

$$(R_1 - z)^2 + (D_m \sin \theta)^2 = R_1^2 \quad (2)$$

Since z is expressed, from FIG. 14:

$$Z = D_m \cos\theta - mp \quad (3)$$

Where p is the pitch of the tracks $17_1$ through $17_m$, the equation (3) is substituted into the equation (2) to yield:

$$D_m^2 = 2D_m \cos\theta(mp + R_1) + (mp)^2 + 2mpR_1 = 0 \quad (4)$$

Therefore, the distance $D_m$ from the middle beam spot $BS_4$ to the beam spot $BS_m$ in the m-th position on the inner side of the beam spot $B_4$ is expressed by solving the quadratic equation (4) as:

$$D_m = \cos\theta(mp + R_1) + \sqrt{R_1^2 - \{\sin\theta(mp + R_1^2)\}} \quad (5)$$

Similarly, the distance $D_m$ from the middle beam spot $BS_4$ to the beam spot $BS_m$ in the m-th position on the outer side of the middle beam spot $BS_4$, expressed as:

$$D_m = -R_1 \cos\theta + \sqrt{(R_1 \cos\theta)_2 + (mp)^2 + 2R_1(mp)} \quad (6)$$

Therefore, the distance $D_m$ from the middle beam spot $BS_4$ to the beam spot $BS_m$ in the m-th position either on the inner side or the outer side of the middle beam spot $BS_4$ can be calculated from the equation (5) or the equation (6). Accordingly, the intervals $l_1$ through $l_6$ of the individual beam spots $BS_1$ through $BS_7$ are obtained as follows. For example, for the radius of curvature $R_1$ of 30 mm, the angle $\theta_1$ of 87 degrees, and the pitch p of 1.5 μm, the intervals 1 through 1 for the beam spots $BS_1$ through $BS_7$, respectively, are calculated as:

$l_1 = 28.8$ μm
$l_2 = 29.0$ μm
$l_3 = 29.8$ μm
$l_4 = 30.4$ μm
$l_5 = 31.0$ μm
$l_6 = 32.3$ μm

Therefore, for the beam spots $BS_1$ through $BS_1$ through $BS_7$ linearly arranged at the angle $\theta$ with respect to the radial direction A of the optical disk 8, in order to position all of the beam spots $BS_1$ through $BS_7$ on the tracks $17_1$ through $17_7$ of the optical disk 8, the intervals $l_1$ through $l_6$ for the beam spots $BS_1$ through $BS_7$ can be calculated as described above. Further, the plurality of laser diode elements $18_1$ through in the laser diode 2 are arranged at the intervals $x_1$ through $x_6$, such that the beam spots $BS_1$ through $BS_7$ are formed at the intervals $l_1$ through $l_6$ (as shown in FIG. 11), while considering the image forming magnification of the image forming optical system 41.

In the above optical system of the present invention, the multibeam optical head can reproduce the information as follows: the laser diode 2 emits the laser beams $LB_1$ through $LB_7$ which are directed onto the tracks $17_1$ through $17_7$ of the optical disk 8, through the image forming optical system 41, along a straight line at the angle $\theta$ with respect to the radial direction A of the optical disk 8 to form the beam spots $BS_1$ through $BS_7$. The beam spots $BS_1$ through $BS_7$ have the intervals $l_1$ through $l_6$ which progressively increases such that each one of the beam spots $BS_1$ through $BS_7$ is positioned on a respective one of the tracks $17_1$ through $17_7$ of the optical disk 8. Therefore, it is possible to accurately and simultaneously position all of the laser beams $LB_1$ through $LB_7$ on the tracks $17_1$ through $17_7$ of the optical disk 8 even when high speed in simultaneously reproducing information from a plurality of tracks of the optical disk is required. In the above embodiment of the present invention, there are a plurality of laser beams. Therefore, when the number of the laser beams is an odd number, it is best to detect a servo signal and particularly a tracking error signal by servo tracking through the middle beam spot $B_4$, since that the differences in the radius of curvature between the tracks at the inner circumference and the outer circumference become larger as the position of the beam spots deviates from the radial direction of the movement of the multibeam optical head, in case the number of the beams is an odd number.

Figure 15:
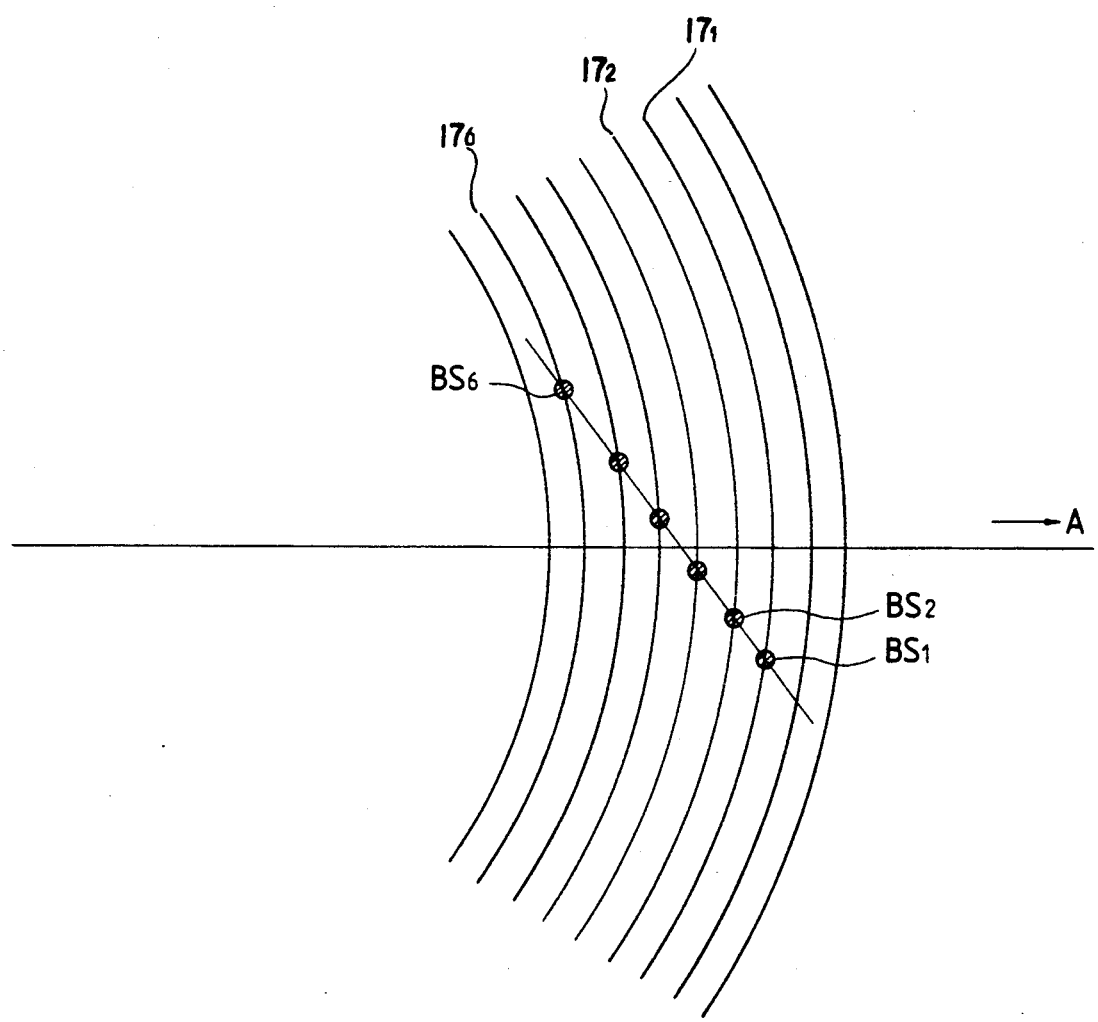
FIG. 15 is a plan view showing the state of image formation with this multibeam in illustration of another embodiment of this invention.

FIG. 15 shows another embodiment of this invention, and a description will now be made of this embodiment, with the same reference numbers being placed on the same parts as in the above described embodiment. In this embodiment, the number of the laser beams is an even number. The number of the beam spots corresponding to the individual laser beams are evenly divided and each divided portion is positioned on a respective one of the two sides with respect to the axis of movement of the multiple optical head.

Figure 16:
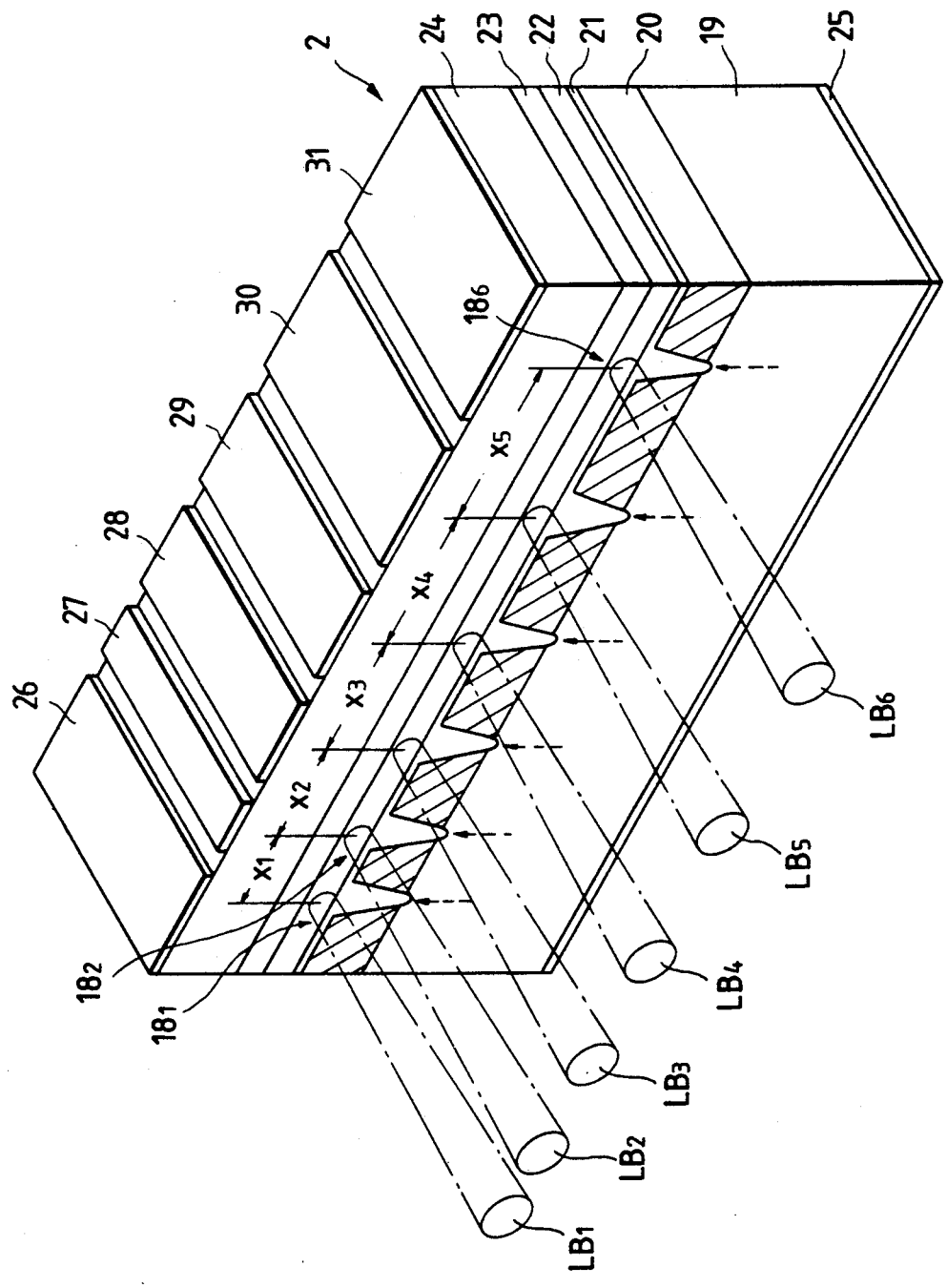
FIG. 16 is a perspective view showing the laser diode.

More specifically, referring to FIG. 16, the laser diode 2 comprises an even number of laser diode elements $18_1$ through $18_6$ (six pieces in the Figure). The laser beams $LB_1$ through $LB_6$ emitted from the laser diode 2 are applied onto the optical disk 8 at the intervals $l_1$ through $l_5$ corresponding to the magnification of the image forming optical system 41 to form the beam spots $BS_1$ through $BS_6$, as shown in FIG. 15.

Figure 17:
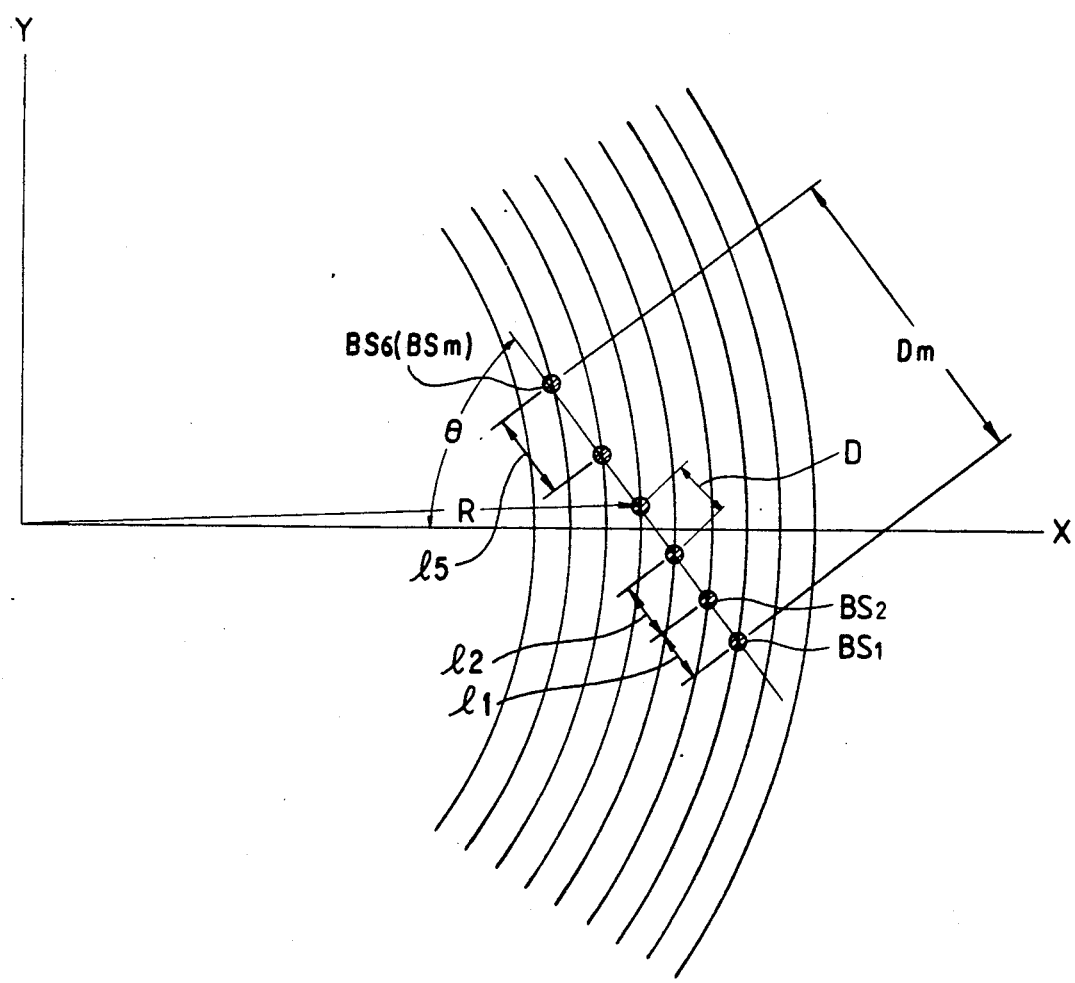
FIG. 17 is an explanatory view showing a method of setting the intervals of the multibeam.

In this case, the two middle beam spots $BS_3$ and $BS_4$ are to move in the radial direction A of the optical disk 8. The intervals $l_1$ through $l_5$ of the individual beam spots $BS_1$ through $BS_6$ are set as shown in FIG. 17. The distance $D_m$ of the individual beam spots $BS_1$ through $BS_6$ is obtained by finding the crossing point of the above equation for a circle expressing the tracks $17_1$ through $17_6$ and the above equation for a straight line expressing the arrangement of the beam spots $BS_1$ through $BS_6$.

Accordingly, by the arithmetic operations performed as mentioned above, the distance $D_m$ from the middle beam spot $BS_4$ to the beam spot $BS_m$ in the m-th position either on the inner side or the outer side from the middle beam spot $BS_4$ is calculated, and the intervals $1_1$ through $1_5$ of the individual beam spots $BS_1$ through $BS_6$ are obtained from this value as shown below. In this regard, for the radius of curvature $R_1$ set at 30 mm, the angle $\theta$ set at 87 degrees, and the pitch p set at 1.6 μm, the intervals $1_1$ through $1_5$ of the individual beam spots $BS_1$ through $BS_6$ are given as follows:

$1_1 = 29.5$ μm
$1_2 = 30.0$ μm
$1_3 = 30.0$ μm
$1_4 = 30.6$ μm
$1_5 = 31.2$ μm

It is thus possible to position all of the beam spots $BS_1$ through $BS_6$ on the tracks $17_1$ through $17_6$ of the optical disk 8, as shown in FIG. 15, by setting the intervals $1_1$ through $1_5$ for the beam spots $BS_1$ through $BS_6$ at the values mentioned above, when the beam spots $BS_1$ through $BS_6$ are arranged in a straight line at the angle $\theta$ with respect to the radial direction A of the optical disk 8.

In the case where the number of the laser beams is an even number, there is no middle beam spot, unlike the case where the number of the laser beams is an odd number. Therefore, in the even number case, the tracking error signal for performing the tracking servo can be taken from either one of the two middle beams closest to the axis of movement of the multibeam optical head 40 or from the mean value of these (what?). The construction and working of the other parts of the system in this embodiment are the same as those of the example of embodiment described above, and their description is therefore omitted here.

This invention consists in the construction and working described above, and, since the laser diode according to this invention is provided with a plurality of light emitting elements arranged at varying intervals, the laser diode is capable of irradiating all of the laser beams emitted from the plurality of light emitting elements onto the tracks on the optical writing media at the same time.

Further, the multibeam optical head according to this invention is so constructed as to be provided with a laser diode in which a plurality of independently drivable light emitting elements are arranged in a straight line with their intervals varied and an image forming optical system which forms images in such a manner that a plurality of laser beams from the laser diode mentioned above are applied onto the optical writing media to form a plurality of beam spots arranged linearly at a prescribed angle in relation to the radial direction of the optical writing media and additionally that the intervals of the plurality of beam spots are varied.

Hence, the multibeam optical head according to this invention is capable of directing each of the plurality of laser beams emitted from the laser diode onto a respective one of the tracks of the optical writing media via the image forming optical system to form the beam spots at the same time even when it is designed to form the beam spots arranged linearly at a prescribed angle to the radial direction of the optical writing media at the same time.

What is claimed is:

1. An optical information system, comprising:
   optical recording means having a plurality of circular tracks uniformly spaced one from another in a radial direction of said optical recording means for recording information thereon; and
   multibeam optical head means optically coupled to said optical recording means and movable along a movement axis in said radial direction, said multibeam optical head means comprising:
      laser diode means having a plurality of lasing means nonuniformly spaced one from another in a straight line for generating a plurality of spaced laser beams, and
      image forming optical means, coupled to said laser diode means, for directing each of said plurality of laser beams onto a respective one of said plurality of tracks of the optical recording means simultaneously to make a beam spot thereon,
      wherein the spacing between adjacent ones of said beam spots corresponds to the spacing between adjacent ones of said lasing means.

2. The optical information system of claim 1, wherein said beam spots are in a straight line inclined at a non-zero angle with respect to said movement axis of the multibeam optical head means.

3. The optical information system of claim 1, wherein the spacing between said adjacent lasing means monotonically increases in the order of the position of said lasing means.

4. The optical information system of claim 1, wherein the number of said plurality of laser beams is an even number.

5. The optical information system of claim 1, wherein the number of said plurality of laser beams is an odd number.

6. The optical information system of claim 1, wherein said laser diode means comprises an odd number of the lasing means.

7. The optical information system of claim 1, wherein said laser diode means comprises an even number of the lasing means.

8. The optical information system of claim 1, said multibeam optical head means further comprising:
   means for reflecting said plurality of laser beams directed on the tracks;
   means, coupled to said reflecting means, for detecting at least one reference laser beam of a plurality of reflected laser beams; and
   means, coupled to said detecting means, for generating a signal corresponding to a detected reference laser beam.

9. The optical information system of claim 1, wherein an equal number of said beam spots are on each side of said movement axis.

10. The optical information system of claim 5, wherein one of said beam spots is on said movement axis.

11. The optical information system of claim 8, wherein said detecting means include a plurality of photodetectors.

12. The optical information system of claim 8, wherein said detecting means includes a pinhole in the center of said detecting means.

13. The optical information system of claim 8, wherein said generating means include a plurality of amplifiers.

* * * * *

UNITED STATES PATENT AND TRADEMARK OFFICE
CERTIFICATE OF CORRECTION

PATENT NO. : 5,144,616
DATED : September 01, 1992
INVENTOR(S) : Kaoru YASUKAWA et al.

It is certified that error appears in the above-identified patent and that said Letters Patent is hereby corrected as shown below:

Abstract, line 13, after "respective" change "tracks" to --track--.

Signed and Sealed this

Ninth Day of November, 1993

Attest:

BRUCE LEHMAN

Attesting Officer

Commissioner of Patents and Trademarks